United States Patent
Liao et al.

(10) Patent No.: US 9,811,000 B2
(45) Date of Patent: Nov. 7, 2017

(54) PHOTOLITHOGRAPHY TOOL AND METHOD THEREOF

(71) Applicant: TAIWAN SEMICONDUCTOR MANUFACTURING CO., LTD., Hsinchu (TW)

(72) Inventors: Chia-Feng Liao, Taichung (TW); Chun-Hsien Lin, Hsinchu (TW); Pei-Yi Su, Taichung (TW); Yi-Ming Dai, Hsinchu (TW); Chung-Hsing Lee, Hsinchu County (TW); Chien-Ko Liao, Taichung (TW); Chun-Yung Chang, Hsinchu (TW); Nan-Jung Chen, Hsinchu (TW); Pei-Yuan Wu, Hsinchu (TW); Hsien-Mao Huang, Hsinchu (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 14/929,098

(22) Filed: Oct. 30, 2015

(65) Prior Publication Data

US 2017/0123328 A1 May 4, 2017

(51) Int. Cl.
*G03B 27/42* (2006.01)
*G03F 7/20* (2006.01)
*G01N 21/88* (2006.01)
*G01N 21/95* (2006.01)

(52) U.S. Cl.
CPC ..... *G03F 7/70483* (2013.01); *G01N 21/8851* (2013.01); *G01N 21/9501* (2013.01)

(58) Field of Classification Search
CPC ............ H01L 21/67259; H01L 21/681; H01L 21/67769; H01L 21/68; H01L 21/68707; H01L 21/67253; H01L 21/67766; H01L 21/67778
See application file for complete search history.

(56) References Cited

U.S. PATENT DOCUMENTS

2008/0055574 A1* 3/2008 Kamono ................ G01N 21/21
355/30
2015/0287625 A1* 10/2015 Fujimoto ............. G01B 11/002
382/151

* cited by examiner

*Primary Examiner* — Mesfin Asfaw
(74) *Attorney, Agent, or Firm* — Maschoff Brennan (57) ABSTRACT

A photolithography tool includes at least one process chamber, at least one front opening unified pod (FOUP) stage, at least one moving mechanism, and an image sensor. The moving mechanism is configured to move the wafer from the process chamber to the FOUP stage. The image sensor is configured to capture the image of the wafer on the moving mechanism.

20 Claims, 6 Drawing Sheets

PHOTOLITHOGRAPHY TOOL AND METHOD THEREOF

BACKGROUND

The present disclosure relates to photolithography tools.

Manufacturing of an integrated circuit (IC) has been driven by increasing the density of the IC formed in a semiconductor device. This is typically accomplished by implementing more aggressive design rules to allow a larger density of the IC device to be formed. Nonetheless, the increased density of IC devices, such as transistors, has also increased the complexity of processing semiconductor devices with decreased feature sizes.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," or "includes" and/or "including" or "has" and/or "having" when used in this specification, specify the presence of stated features, regions, integers, operations, operations, elements, and/or components, but do not preclude the presence or addition of one or more other features, regions, integers, operations, operations, elements, components, and/or groups thereof.

Furthermore, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1A:
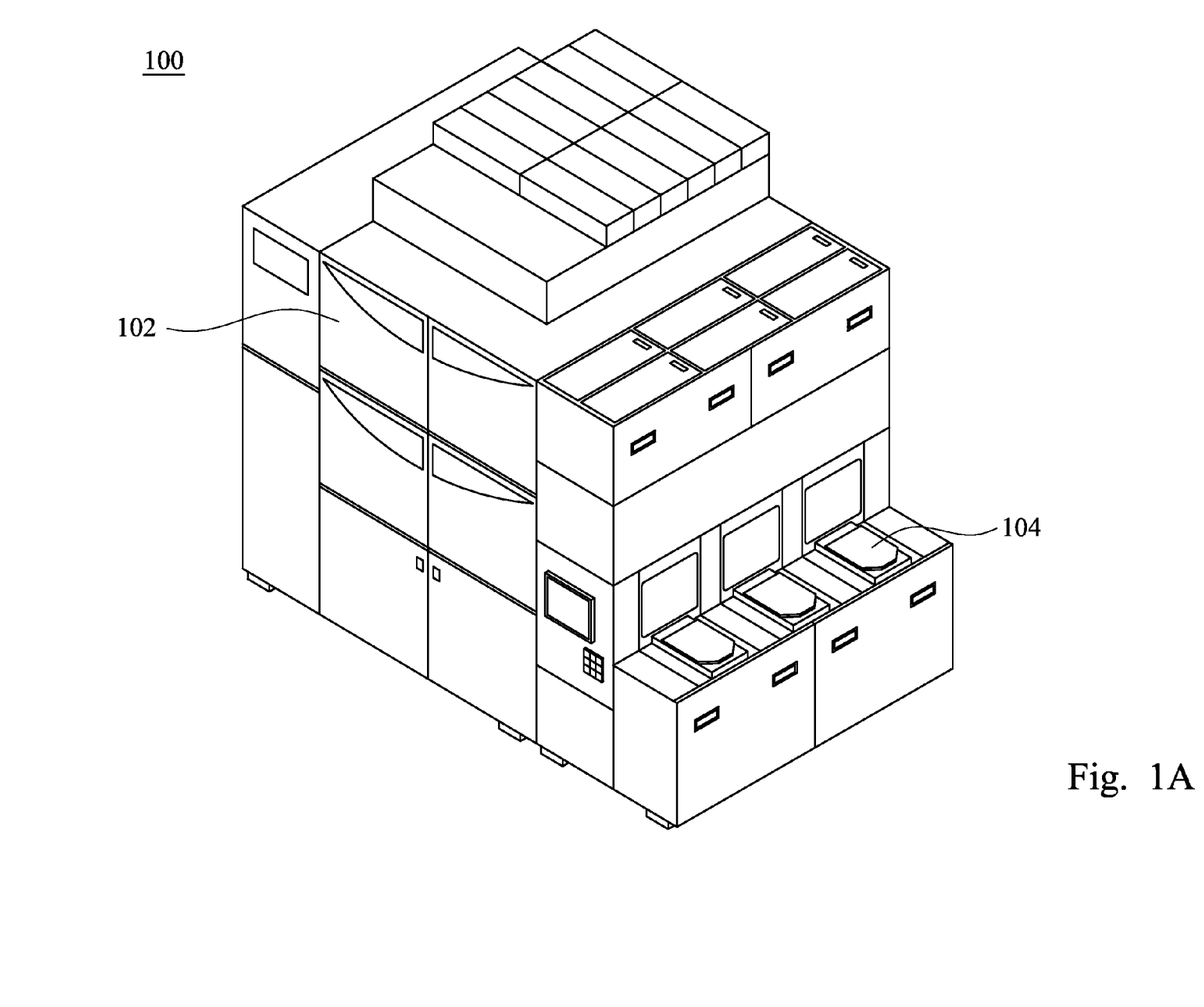
FIG. 1A is a perspective view of a photolithography tool in accordance with some embodiments of the present disclosure.
Figure 1B:
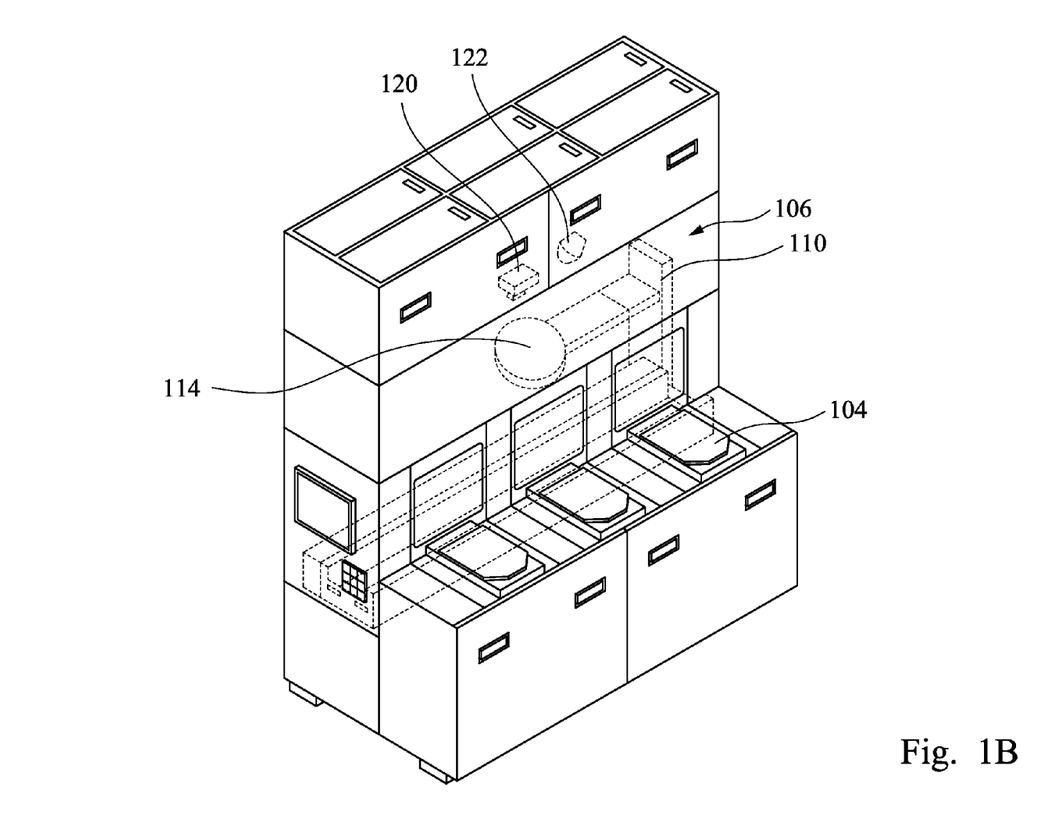
FIG. 1B is a perspective view of a photolithography tool and a transportation space thereof in accordance with some embodiments of the present disclosure.

Reference is made to FIGS. 1A and 1B. FIG. 1A is a perspective view of a photolithography tool 100 in accordance with some embodiments of the present disclosure. FIG. 1B is a perspective view of a photolithography tool 100 and a transportation space 106 thereof in accordance with some embodiments of the present disclosure. A photolithography tool 100 includes at least one process chamber 102, at least one front opening unified pod (FOUP) stage 104, at least one transportation space 106, at least one moving mechanism 110, and an image sensor 120. The transportation space 106 communicates the FOUP stage 104 with the process chamber 102. The moving mechanism 110 is present in the transportation space 106 and is configured to move at least one wafer 114 from the process chamber 102 to the FOUP stage 104. The image sensor 120 is present in the transportation space 106 and is configured to capture an image of the wafer 114 on the moving mechanism 110.

In some embodiments, the number of the process chambers 102 of the photolithography tool 100 is plural, such that various processes are performed on the wafer 114 placed in the photolithography tool 100. Thus, the wafer 114 placed in the photolithography tool 100 is processed by the various processes in the corresponding process chambers 102. In various embodiments, the image sensor 120 is configured to capture an image of the wafer 114 after the wafer 114 is processed by one or more of the various processes, so as to determine whether the processes performed on the wafer 114 are acceptable. Explained in a different way, by capturing the image of the wafer 114, a determination is made as to whether the processes performed on the wafer 114 are acceptable.

Thus, after the operations of capturing the image of the wafer and determining whether the processes performed on the wafer are acceptable, the wafer, if determined to be acceptable, is moved to a subsequent process tool or chamber, thereby improving the yield rate of the wafer fabrication. In addition, in some embodiments, any wafer that is determined as being unacceptable is moved out of the manufacturing process, such that the cost of manufacture is reduced since subsequent processes are not performed on such wafers deemed unacceptable.

Furthermore, in some embodiments, the operation of capturing the image of the wafer 114 is performed when the wafer 114 is moved from the process chamber 102 to the FOUP stage 104. Thus, the operations of moving the wafer 114 from the process chamber 102 to the FOUP stage 104 and capturing the image of the wafer 114 are performed simultaneously. As a result of performing the operations of moving the wafer 114 and capturing the image of the wafer 114 simultaneously, the time for performing the processes with the wafer 114, which include determining whether the processes performed on the wafer 114 are acceptable, is reduced, thereby improving process efficiency.

Figure 2:
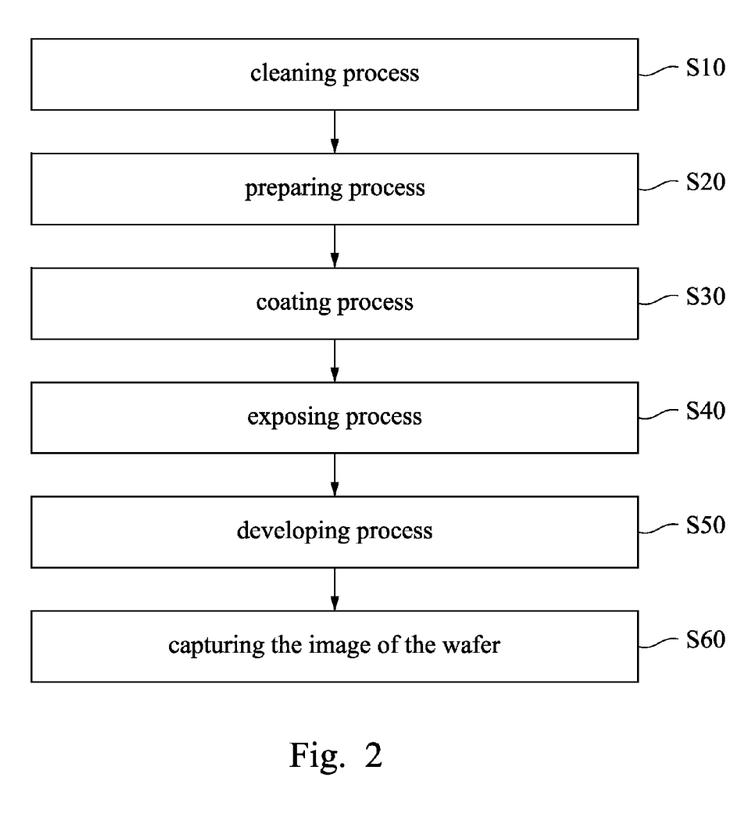
FIG. 2 is a flowchart of operations performed on a wafer in a photolithography tool in accordance with some embodiments of the present disclosure.

Operations performed on a wafer in a photolithography tool will be described in greater detail with additional reference to FIG. 2. FIG. 2 is a flowchart of operations S10-S60 performed on a wafer in a photolithography tool in accordance with some embodiments of the present disclosure. As previously described, the number of the process chambers 102 (see FIG. 1A) of the photolithography tool 100 is plural, and hence, various processes are performed on the wafer. In some embodiments, a combination of the various processes is a photolithography method and the various processes at least include a coating process, an exposing process, and a developing process, in which the operation of capturing the image of the wafer described above is performed after the developing process. Furthermore, in various embodiments, the various processes further include a pre-treatment process before the coating process. In such embodiments in which the various processes further include the pre-treatment process before the coating process, the pre-treatment process includes a cleaning process and a preparing process. The cleaning process, the preparing process, the coating process, the exposing process, the developing process, and the operation of capturing the image of the wafer are shown as operations S10-S60 in FIG. 2.

In the operation S10, a cleaning process is performed with the wafer, in which a wet chemical treatment is used to remove organic or inorganic contaminants present on the wafer surface. For example, an RCA clean procedure based on solutions containing hydrogen peroxide is used, in which the RCA clean procedure is a set of wafer cleaning steps performed before high-temperature processing steps. In such embodiments where a wet chemical treatment is used, other solutions made with trichloroethylene, acetone or methanol are used to perform cleaning.

In the operation S20, a preparing process is performed with the wafer, in which the wafer is initially heated to a temperature sufficient to remove moisture that is present on the wafer surface. In some embodiments, a liquid or gaseous adhesion promoter is applied to promote adhesion of a photoresist to the wafer, such as Bis(trimethylsilyl)amine (also known as hexamethyldisilazane, or HMDS). The surface layer of silicon dioxide on the wafer reacts with HMDS to form tri-methylated silicon-dioxide, which is a water repellent layer. This water repellent layer prevents the aqueous developer from penetrating between the photoresist and the wafer surface, thus preventing so-called lifting of small photoresist structures in the (developing) pattern. In various embodiments, in order to ensure the development of the pattern, the wafer with the adhesion promoter is placed over a hot plate and is heated for drying.

In the operation S30, a coating process is performed with the wafer, in which the coating process includes forming a photoresist on the wafer in accordance with some embodiments. In some embodiments, the operation of forming the photoresist on the wafer further includes applying the photoresist on the wafer. In such embodiments including applying the photoresist on the wafer, the wafer is covered with the photoresist by a spin coating process. Thus, a viscous liquid solution of the photoresist is dispensed onto the wafer, and the wafer is spun rapidly to produce a uniformly thick layer. The spin coating process results in a uniform thin layer thereon. This uniformity is explained by detailed fluid-mechanical modeling, which shows that the photoresist moves much faster at the top of the layer than at the bottom, where viscous forces bind the photoresist to the wafer surface. Explained in a different way, the top layer of the photoresist is quickly ejected from the wafer edge while the bottom layer creeps slowly and radially along the wafer. In addition, a final thickness of the photoresist is also determined by the evaporation of liquid solvents from the photoresist. In various embodiments, the photoresist-coated wafer is then prebaked to remove excess photoresist solvent on a hotplate.

In the operation S40, an exposing process is performed with the wafer, in which the exposing process includes exposing the photoresist to a pattern of light in accordance with some embodiments. In such embodiments involving exposing the photoresist to a pattern of light, the photoresist is exposed to a pattern of intense light after prebaking. The exposure to light causes a chemical change that allows some of the photoresist to be removed by a solution, which is referred to as a developer. With such operations, a positive photoresist becomes soluble in the developer when exposed. On the other hand, a negative photoresist with unexposed regions is soluble in the developer. In some embodiments, a post-exposure bake is performed before developing to reduce standing wave phenomena caused by the destructive and constructive interference patterns of the incident light. In some embodiments, in deep ultraviolet lithography, chemically amplified resist chemistry is used.

In the operation S50, a developing process is performed with the wafer, in which the developing process includes developing the exposed photoresist. In such embodiments involving developing the exposed photoresist, the develop agent is delivered on a spinner, much like a photoresist. In various embodiments, the developer includes sodium hydroxide, and metal-ion-free developers such as tetramethylammonium hydroxide are used. Furthermore, in some embodiments, a postbake process is used after the developing process, in which the postbake process is used to harden the final resist pattern of the photoresist. In the postbake process, the resin polymer in the photoresist is processed to cross-link under a high temperature. The temperature at which flow begins is related to the glass transition temperature and is a measure of the thermal stability of the photoresist. In addition to cross-linking, the postbake process removes residual solvent, water, and gasses, and improves adhesion of the photoresist to the wafer.

In the operation S60, the operation of capturing the image of the wafer is performed, in which the operation of capturing the image of the wafer is performed after the developing process in accordance with some embodiments. In some embodiments, after performing the developing process, the operation of capturing the image of the wafer by the image sensor is performed to determine whether the wafer processed with the various processes or the photoresist thereon is acceptable. The following description is provided to explain the determination of whether the wafer processed with the various processes or the photoresist thereon is acceptable.

Figure 3:
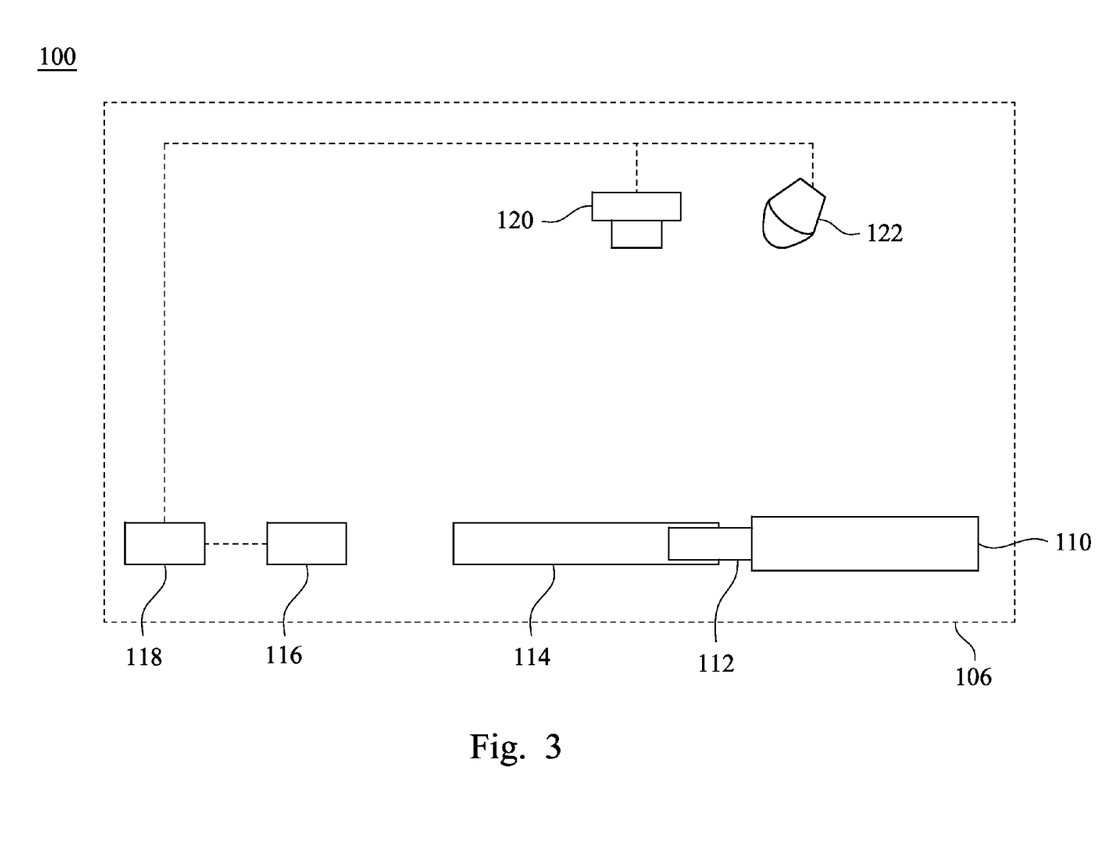
FIG. 3 is a schematic diagram of a configuration in a transportation space of a photolithography tool in accordance with some embodiments of the present disclosure.

FIG. 3 is a schematic diagram of a configuration in a transportation space 106 of a photolithography tool 100 in accordance with some embodiments of the present disclosure. Referring to FIGS. 1B and 3, in some embodiments, after the wafer 114 is processed by one or more of the various processes, the wafer 114 is moved from one of the process chambers 102 (see FIG. 1A) to the FOUP stage 104 by the moving mechanism 110. In some embodiments, the moving mechanism 110 is a robot arm, and the moving mechanism 110 includes a holder 112 configured to hold the wafer 114. In some embodiments, since the photolithography tool 100 includes the transportation space 106 communicating the FOUP stage 104 with the process chamber 102 (see FIG. 1A), the wafer 114 is moved to pass through the transportation space 106 by the moving mechanism 110.

In some embodiments, the image sensor 120 is an area image sensor. Thus, after the developing process, the image of the wafer 114 is captured by the image sensor 120 through an area scanning process. In the area scanning process, a plurality of parts of the image of the wafer 114 are captured by the image sensor 120, and then the whole image of the wafer is formed by combining the parts of the image of the wafer 114 in accordance with some embodiments. In the other embodiments of capturing the image with the area scanning process, an image of the entire wafer 114 is captured by the image sensor 120 in one shot. In this case, the time for capturing the image of the wafer 114 is reduced, thereby improving process efficiency. In addition, in some embodiments, the image sensor 120 is a charge-coupled device (CCD) or an active-pixel sensor (APS).

In some embodiments, the photolithography tool 100 further includes a light source 122 configured to illuminate the wafer 114 on the moving mechanism 110. In such embodiments in which the light source 122 is configured to illuminate the wafer 114 on the moving mechanism 110, the light source 122 is present in the transportation space 106. During moving the wafer 114 in the transportation space 106, the image of the wafer 114 is captured by the image sensor 120, and the wafer 114 is illuminated when the operation of capturing the image is performed in accordance with some embodiments. Explained in a different way, the operations of capturing the image of the wafer 114 and illuminating the wafer 114 are performed simultaneously. In some embodiments, the light source 122 is configured to provide light with a wavelength greater than about 365 nm, so as to reduce damage to the wafer 114 by the light. In such embodiments in which the wavelength of light is greater than about 365 nm, the wavelength band of the light is within an infrared band including a near-infrared (NIR) band, a mid-infrared (MIR) band, and a far-infrared (FIR) band. In the other embodiments, the wavelength band of the light is within a visible spectrum.

In some embodiments, the photolithography tool 100 further includes a detector 116 and an actuator 118. The detector 116 is configured to detect whether the wafer 114 is present within a field of view of the image sensor 122. In some embodiments, the detector 116 is a height level detector configured to detect the height of the moving mechanism 110. The actuator 118 is configured to actuate the image sensor 122 to capture the image of the wafer 114 when the wafer 114 is detected to be present within the field of view of the image sensor 122. In addition, the actuator 118 is also configured to actuate the light source 122 to illuminate the wafer 114 on the moving mechanism 110. Furthermore, the detector 116 is electrically connected to the actuator 118, and the actuator 118 is electrically connected to the image sensor 122. In the embodiments in which the detector 116 and the actuator 118 are used, the detector 116 is disposed in the transportation space 106, and the field of view of the image sensor 122 is a pre-determined position in the transportation space 106. With this configuration, when the wafer 114 is moved from one of the process chambers 102 (see FIG. 1A) to the transportation space 106, the wafer 114 is detected by the detector 116, and a signal is transmitted from the detector 116 to the actuator 118. After receiving the signal, the actuator 118 actuates the image sensor 122 to capture the image of the wafer 114. Thus, a combination of the detector 116, the actuator 118, and the image sensor 122 performs an operation of detecting whether the wafer 114 leaves the process chamber 102 (see FIG. 1A) or enters the transportation space 106, in which the operation of capturing the image of the wafer 114 is performed after the wafer 114 is detected to have left the process chamber 102 (see FIG. 1A) or to have entered the transportation space 106.

Figure 4:
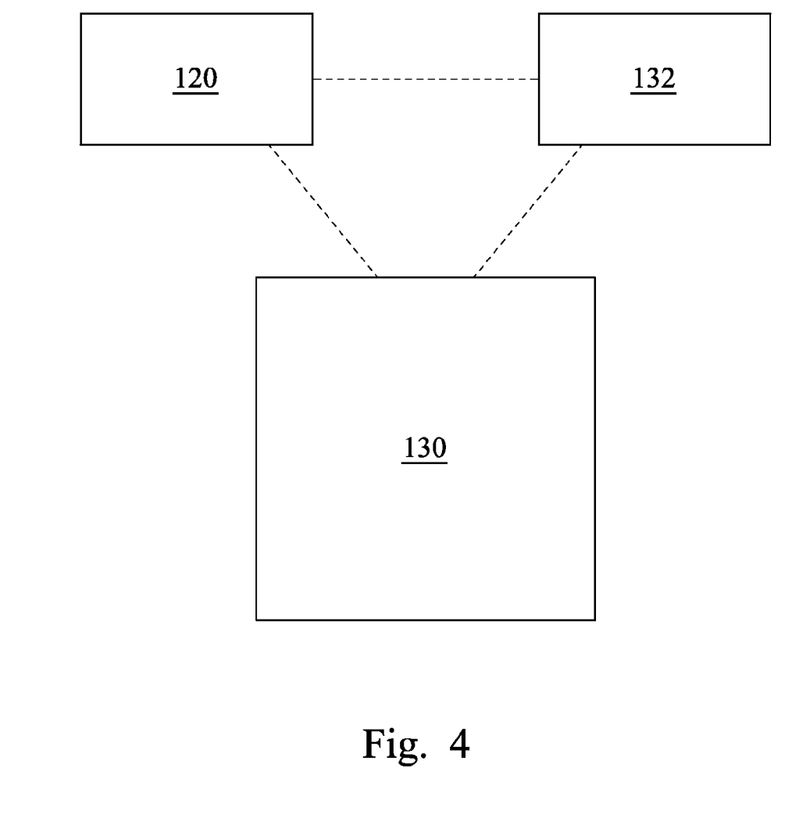
FIG. 4 is a schematic block diagram of an image sensor, a server computer system, and a processing unit in accordance with some embodiments of the present disclosure.

Reference is made to FIGS. 3 and 4. FIG. 4 is a schematic block diagram of an image sensor 120, a server computer system 130, and a processing unit 132 in accordance with some embodiments of the present disclosure. In some embodiments, the photolithography tool further 100 includes a server computer system 130 electrically coupled to the image sensor 120. In some embodiments, the image of the wafer 114 captured by the image sensor 120 is uploaded to the server computer system 130, and the server computer system 130 is configured to store the image of the wafer 114 captured by the image sensor 120 therein. In such embodiments in which the images are uploaded to the server computer system 130, the image sensor 120 includes a transmitter (not shown) and the server computer system 130 includes a receiver (not shown), in which the transmitter and the receiver are coupled to each other. In some embodiments, the image of the wafer 114 captured by the image sensor 120 is uploaded to the server computer system 130 through a wireless communication network. Furthermore, in some embodiments, a plurality of the images of the various wafers are saved in the server computer system 130. Hence, the state of each of the various wafers after the developing process is recorded in the server computer system 130.

In some embodiments, the photolithography tool 100 further includes a processing unit 132 electrically connected to the image sensor 120. The processing unit 132 is configured to compare the image of the wafer 114 with a reference image and determine whether the wafer 114 is acceptable based on the comparison between the image of the wafer 114 and the reference image. Explained in a different way, after the operation of capturing the image of the wafer 114 has been performed, the processing unit 132 is programmed to compare this image of the wafer 114 with the reference image, and then the processing unit 132 determines whether the wafer 114 is acceptable.

In some embodiments, the reference image includes an image of a wafer with acceptable performance. In various embodiments, the image of the wafer 114 is compared with the reference image with acceptable performance using a comparison rate in a range from about 15% to about 25%. That is, if a percentage of similarity between the image of the wafer 114 and the reference image with acceptable performance is more than a rate in a range from about 75% to about 85%, the processed wafer 114 is taken as being acceptable. In some embodiments, the image sensor 120 includes a transmitter (not shown) and the processing unit 132 includes a receiver (not shown), in which the transmitter and the receiver are coupled to each other. In some embodiments, the image of the wafer 114 captured by the image sensor 120 is uploaded to the processing unit 132 through a wireless communication network. Alternatively, the processing unit 132 is disposed to electrically connect to the image sensor 120 with a data line or is disposed in the image sensor 120.

In some embodiments, the reference image includes an image of another wafer (i.e., a wafer that is different from the wafer 114 that is undergoing an acceptable determination process). For example, as a plurality of the wafers are processed, the processing unit 132 compares the difference between the wafers processed in the same operation (or the wafers processed under the same condition). Furthermore, in some embodiments, the processing unit 132 is electrically connected to the server computer system 130. In some embodiments, a plurality of the processing units 132 are electrically connected to the image sensor 120 or the server computer system 130, so as to improve the efficiency of the comparison. Thus, the operations of comparing the image of the wafer 114 with the reference image and determining whether the wafer 114 is acceptable are performed quickly and effectively. Therefore, with the plural processing units 132, the operation of determining whether the wafer 114 is acceptable is completed before the wafer 114 reaches the FOUP stage 104 (see FIG. 1B).

Figure 5:
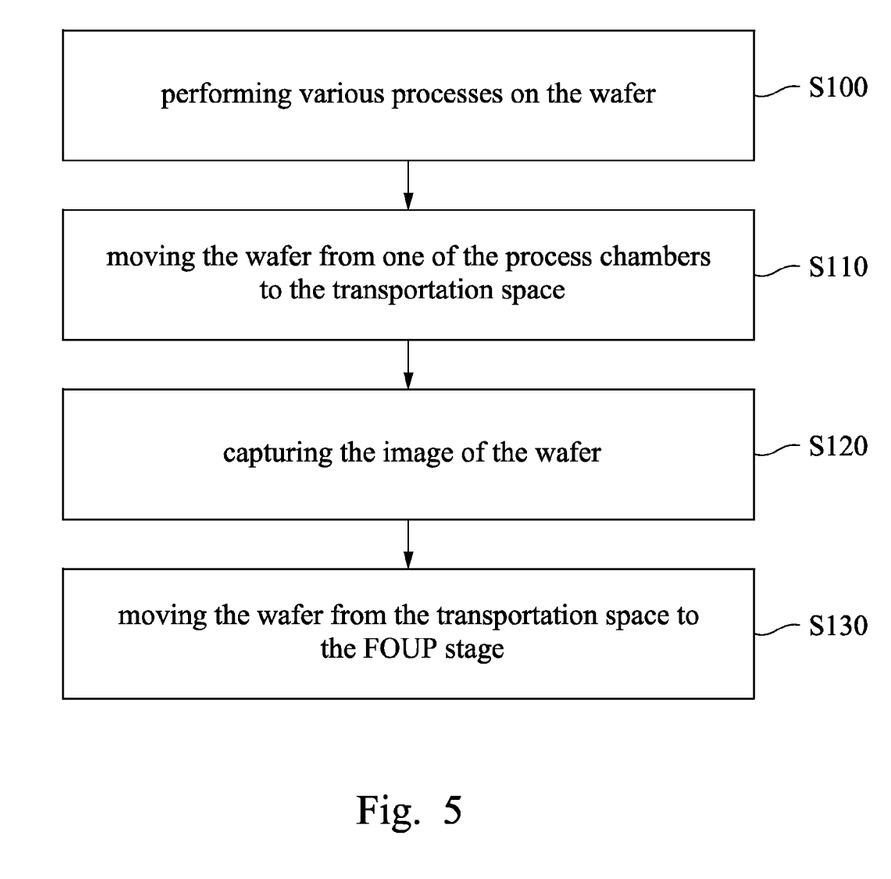
FIG. 5 is a flowchart of operations performed on a wafer in a photolithography tool in accordance with some embodiments of the present disclosure.

Reference is made to FIG. 5. FIG. 5 is a flowchart of operations S100-S130 performed on a wafer in a photolithography tool in accordance with some embodiments of the present disclosure. In some embodiments, operations S100-S130 are performed on a wafer placed in the photolithography tool. The operation S100 involves performing various processes on the wafer. The operation S110 involves moving the wafer from one of the process chambers to the transportation space. The operation S120 involves capturing the image of the wafer. The operation S130 involves moving the wafer from the transportation space to the FOUP stage. Each of the operations S100-S130 will be described in greater detail below.

In the operation S100, the wafer placed in the photolithography tool is moved to one of the process chambers. In some embodiments, the wafer is processed by the pre-treatment process, the coating process, the exposing process, and the developing process in sequence, in which the pre-treatment process includes the cleaning process and the preparing process. Therefore, after the operation S100, the photoresist with the pattern is formed on the wafer.

In the operation S110, the wafer is moved from one of the process chambers to the transportation space by the moving mechanism. In some embodiments, the wafer with the patterned photoresist thereon is moved from the developing chamber to the FOUP stage, in which the wafer is in the transportation space after leaving the developing chamber.

In the operation S120, the image of the wafer in the transportation space is captured by the image sensor, in which the operations of moving the wafer and capturing the image are performed simultaneously in accordance with some embodiments. In various embodiments, after the wafer is moved into the transportation space, the operation of detecting whether the wafer is present within the field of view of the image sensor is performed, in which the operation of detecting is performed by the detector. Under the situation that the wafer is present within the field of view of the image sensor, the image sensor is actuated to capture the image of the wafer by the actuator. In some embodiments, the images of the wafer and the patterned photoresist thereon are captured together by the image sensor. In some embodiments, at least one of the images of the wafer and the patterned photoresist thereon are captured by the image sensor. After the image of the wafer or the patterned photoresist thereon is captured, the image of the wafer is compared with the reference image by the processing unit, and then the processing unit determines whether the wafer is acceptable based on the comparison between the image of the wafer and the reference image. In some embodiments, the operation of determining whether the wafer is acceptable includes an operation of determining whether the patterned photoresist formed on the wafer is acceptable. In various embodiments, the operation of detecting whether the wafer is present within the field of view of the image sensor, the operation of actuating the image sensor to capture the image of the wafer, the operation of capturing the image of the wafer, the operation of comparing the image of the wafer with the reference image, and the operation of determining whether the wafer is acceptable based on the comparison process are performed in sequence. Furthermore, in some embodiments, the operation of illuminating the wafer is performed simultaneously with the operation of capturing the image of the wafer.

In the operation S130, the wafer, after the determination as to whether the wafer is acceptable, is moved from the transportation space to the FOUP stage. In some embodiments, after the wafer is determined to be acceptable, the wafer is moved to a subsequent process. For example, the subsequent process includes an etching process.

As described above, the image of the wafer after the various processes is captured by the image sensor, so as to determine whether the wafer is acceptable. After the operations of capturing the image of the wafer and determining whether the wafer is acceptable, the wafer determined as being acceptable is moved to the subsequent process tool or chamber, thereby improving the yield rate of the wafer in the subsequent processes. In addition, the wafer determined as being unacceptable is moved out of the manufacturing process, such that the cost of manufacture is reduced since the subsequent processes are performed with the wafer determined as being acceptable. Furthermore, since the operations of moving the wafer from the process chamber to the FOUP stage and capturing the image of the wafer are performed simultaneously, the time for performing the various processes with the wafer in the photolithography tool is reduced, thereby improving process efficiency.

According to various embodiments of the present disclosure, the photolithography tool is provided. The photolithography tool includes the process chamber, the FOUP stage, the moving mechanism, and the image sensor. The moving mechanism is configured to move the wafer from the process chamber to the FOUP stage. The image sensor is configured to capture the image of the wafer on the moving mechanism.

According to various embodiments of the present disclosure, the photolithography tool is provided. The photolithography tool includes the process chamber, the FOUP stage, the transportation space communicating the FOUP stage with the process chamber, the moving mechanism, and the image sensor. The moving mechanism is present in the transportation space. The image sensor is present in the transportation space.

According to various embodiments of the present disclosure, the photolithography method is provided. The method includes the operations of forming the photoresist on the wafer in the process chamber, moving the wafer from the process chamber to the FOUP stage, and capturing the image of the wafer when the wafer is moved from the process chamber to the FOUP stage.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A photolithography tool, comprising:
   at least one process chamber;
   at least one front opening unified pod (FOUP) stage;
   at least one moving mechanism configured to move at least one wafer from the process chamber to the FOUP stage;
   an image sensor configured to capture an image of the wafer on the moving mechanism;
   a detector configured to detect whether the wafer is present within a field of view of the image sensor; and
   an actuator configured to actuate the image sensor to capture the image of the wafer when the wafer is detected to be present within the field of view of the image sensor.

2. The photolithography tool of claim 1, further comprising:
   a light source configured to illuminate the wafer on the moving mechanism.

3. The photolithography tool of claim 2, wherein the actuator is configured to actuate the light source to illuminate the wafer on the moving mechanism.

4. The photolithography tool of claim 1, wherein the image sensor is an area image sensor.

5. The photolithography tool of claim 1, wherein the image sensor is a charge-coupled device (CCD) or an active-pixel sensor (APS).

6. The photolithography tool of claim 1, further comprising:
   a processing unit configured to compare the image of the wafer with a reference image and determine whether the wafer is acceptable based on the comparison between the image of the wafer and the reference image.

7. The photolithography tool of claim 1, wherein the process chamber is configured to form a photoresist on the wafer, and the image sensor is configured to capture the image of the wafer with the photoresist thereon.

8. A photolithography tool, comprising:
   at least one process chamber;
   at least one front opening unified pod (FOUP) stage;
   at least one transportation space communicating the FOUP stage with the process chamber;
   at least one moving mechanism present in the transportation space;
   an image sensor present in the transportation space;
   a detector configured to detect whether a wafer is present within the transportation space; and
   an actuator configured to actuate the image sensor to capture an image of the wafer when the wafer is detected to be present within the transportation space.

9. The photolithography tool of claim 8, further comprising:
   a light source present in the transportation space.

10. The photolithography tool of claim 9, wherein the light source is configured to provide light with a wavelength greater than about 365 nm.

11. The photolithography tool of claim 8, wherein the image sensor is an area image sensor.

12. The photolithography tool of claim 8, wherein the image sensor is a charge-coupled device (CCD) or an active-pixel sensor (APS).

13. The photolithography tool of claim 8, further comprising:
   a processing unit electrically connected to the image sensor, wherein the image sensor is configured to capture an image of the wafer in the transportation space, and the processing unit is programmed to compare the image of the wafer with a reference image and determine whether the wafer is acceptable based on the comparison between the image of the wafer and the reference image.

14. The photolithography tool of claim 8, wherein the detector is in the transportation space.

15. A photolithography method, comprising:
   forming a photoresist on a wafer in at least one process chamber;
   moving the wafer from the process chamber to a front opening unified pod (FOUP) stage;
   detecting whether the wafer is present within a field of view of an image sensor; and
   capturing an image of the wafer by the image sensor when the wafer is moved from the process chamber to the FOUP stage and when the wafer is detected to be present within the field of view of the image sensor.

16. The photolithography method of claim 15, further comprising:
   illuminating the wafer when performing the capturing of the image of the wafer.

17. The photolithography method of claim 15, wherein the forming the photoresist on the wafer comprises:
   applying the photoresist on the wafer;
   exposing the photoresist to a pattern of light; and
   developing the exposed photoresist, wherein the capturing the image of the wafer is performed after the developing the exposed photoresist.

18. The photolithography method of claim 15, further comprising:
   detecting whether the wafer leaves the process chamber, wherein the capturing the image of the wafer is performed after the wafer is detected to have left the process chamber.

19. The photolithography method of claim 15, further comprising:
   comparing the image of the wafer with a reference image; and
   determining whether the wafer is acceptable based on the comparing the image of the wafer.

20. The photolithography method of claim 15, wherein the capturing the image of the wafer comprises:
   capturing a plurality of parts of the image of the wafer; and
   combining the parts of the image of the wafer to form a whole image of the wafer.

* * * * *